(12) United States Patent
Genta et al.

(10) Patent No.: US 9,238,827 B2
(45) Date of Patent: *Jan. 19, 2016

(54) BIOMASS HYDROTHERMAL DECOMPOSITION APPARATUS AND METHOD

(75) Inventors: Minoru Genta, Hyogo (JP); Ryosuke Uehara, Hyogo (JP); Kinya Fujita, Hyogo (JP); Setsuo Omoto, Hiroshima (JP); Wataru Matsubara, Hiroshima (JP); Yoshio Seiki, Tokyo (JP)

(73) Assignee: MITSUBISHI HEAVY INDUSTRIES MECHATRONICS SYSTEMS, LTD., Hyogo (JP)

(*) Notice: Subject to any disclaimer, the term of this patent is extended or adjusted under 35 U.S.C. 154(b) by 0 days.

This patent is subject to a terminal disclaimer.

(21) Appl. No.: 12/438,792

(22) PCT Filed: Sep. 19, 2008

(86) PCT No.: PCT/JP2008/067040
§ 371 (c)(1),
(2), (4) Date: Feb. 25, 2009

(87) PCT Pub. No.: WO2009/096062
PCT Pub. Date: Aug. 6, 2009

(65) Prior Publication Data
US 2010/0285574 A1 Nov. 11, 2010

(30) Foreign Application Priority Data
Feb. 1, 2008 (JP) .................................. 2008-023186

(51) Int. Cl.
*C12P 7/00* (2006.01)
*C12P 7/10* (2006.01)
(Continued)

(52) U.S. Cl.
CPC ............... *C12P 7/10* (2013.01); *B01D 11/0226* (2013.01); *B09B 3/00* (2013.01); *C08B 37/0057* (2013.01);
(Continued)

(58) Field of Classification Search
USPC .......... 435/290.1, 290.2, 290.4, 291.1, 291.5, 435/291.7; 71/11, 14, 15; 162/1, 223, 234, 162/244, 248, 250; 241/20, 21, 28, 38
See application file for complete search history.

(56) References Cited

U.S. PATENT DOCUMENTS 3,833,461 A * 9/1974 Woodruff .................... 162/19
3,985,728 A 10/1976 Lin
(Continued)

FOREIGN PATENT DOCUMENTS

CA   2 448 862 A1   9/2002
CA   2654306 A1     8/2009
(Continued)

OTHER PUBLICATIONS le;.5qEnglish translation of JP 2007-301472 to Nakagame et al.*
(Continued)

*Primary Examiner* — Nathan Bowers
(74) *Attorney, Agent, or Firm* — Westerman, Hattori, Daniels & Adrian, LLP

(57) ABSTRACT

A biomass hydrothermal decomposition apparatus includes, a biomass feeder (31) that feeds biomass material (11) under normal pressure to under increased pressure, a hydrothermal decomposition device (41A) that allows the fed biomass material (11) to be gradually moved inside a gradient device main body (42) from a lower end thereof with a conveyor screw (43), and also allows hot compressed water (15) to be fed from an other end of a feed section (31) for the biomass material into the main body (42), so as to cause the biomass material (11) and the hot compressed water (15) to countercurrently contact with each other and undergo hydrothermal decomposition, and that transfers a lignin component and a hemicellulose component into the hot compressed water, so as to separate the lignin component and the hemicellulose component from the biomass material (11); and a biomass discharger (51) that discharges, from the upper end of the device main body (42), a biomass solid residue (17) under increased pressure to an under normal pressure.

8 Claims, 6 Drawing Sheets

(51) Int. Cl.

| | |
|---|---|
| *B01D 11/02* | (2006.01) |
| *B09B 3/00* | (2006.01) |
| *C08B 37/00* | (2006.01) |
| *C08H 7/00* | (2011.01) |
| *C08H 8/00* | (2010.01) |
| *C10G 1/02* | (2006.01) |
| *C10G 1/04* | (2006.01) |
| *C10L 5/44* | (2006.01) |
| *C10L 9/08* | (2006.01) |
| *C12M 1/00* | (2006.01) |
| *C12M 1/33* | (2006.01) |
| *B01D 11/00* | (2006.01) |

(52) U.S. Cl.
CPC .. *C08H 6/00* (2013.01); *C08H 8/00* (2013.01); *C10G 1/02* (2013.01); *C10G 1/047* (2013.01); *C10L 5/44* (2013.01); *C10L 9/086* (2013.01); *C12M 21/12* (2013.01); *C12M 45/02* (2013.01); *C12M 45/20* (2013.01); *B01D 2011/002* (2013.01); *Y02E 50/10* (2013.01); *Y02E 50/16* (2013.01); *Y02E 50/30* (2013.01)

(56) References Cited

U.S. PATENT DOCUMENTS

| | | | |
|---|---|---|---|
| 4,023,982 | A | 5/1977 | Knauth |
| 4,152,197 | A * | 5/1979 | Lindahl et al. .................. 162/19 |
| 4,443,540 | A | 4/1984 | Chervan et al. |
| 4,650,689 | A | 3/1987 | Hedrick |
| 4,746,401 | A | 5/1988 | Roberts et al. |
| 4,859,322 | A | 8/1989 | Huber |
| 5,348,871 | A | 9/1994 | Scott et al. |
| 5,411,594 | A | 5/1995 | Brelsford |
| 5,424,417 | A | 6/1995 | Torget et al. |
| 5,466,108 | A | 11/1995 | Piroska |
| 5,846,787 | A * | 12/1998 | Ladisch et al. ................. 435/99 |
| 6,022,419 | A | 2/2000 | Torget et al. |
| 6,039,774 | A * | 3/2000 | McMullen et al. ......... 48/102 A |
| 6,419,788 | B1 | 7/2002 | Wingerson |
| 8,123,864 | B2 | 2/2012 | Christensen et al. |
| 8,163,517 | B2 | 4/2012 | Genta et al. |
| 9,102,956 | B2 | 8/2015 | Genta et al. |
| 2002/0151034 | A1 | 10/2002 | Zhang et al. |
| 2006/0280663 | A1* | 12/2006 | Osato et al. .................. 422/226 |
| 2007/0231869 | A1 | 10/2007 | Holmgren et al. |
| 2007/0259412 | A1 | 11/2007 | Belanger et al. |
| 2008/0026431 | A1 | 1/2008 | Saito et al. |
| 2008/0028675 | A1 | 2/2008 | Clifford, III et al. |
| 2008/0032344 | A1* | 2/2008 | Fallavollita .................... 435/72 |
| 2008/0044891 | A1 | 2/2008 | Kinley et al. |
| 2008/0299628 | A1 | 12/2008 | Hallberg et al. |
| 2009/0077729 | A1* | 3/2009 | McLeod ........................... 4/300 |
| 2009/0283397 | A1* | 11/2009 | Kato et al. .................... 202/208 |
| 2010/0108567 | A1 | 5/2010 | Medoff |
| 2010/0184176 | A1* | 7/2010 | Ishida et al. .................. 435/165 |
| 2010/0269990 | A1 | 10/2010 | Dottori et al. |
| 2010/0285574 | A1 | 11/2010 | Genta et al. |
| 2010/0330638 | A1 | 12/2010 | Aita et al. |
| 2011/0003348 | A1 | 1/2011 | Genta et al. |
| 2011/0079219 | A1 | 4/2011 | McDonald et al. |
| 2011/0314726 | A1 | 12/2011 | Jameel et al. |
| 2012/0006320 | A1 | 1/2012 | Nguyen |
| 2012/0315683 | A1 | 12/2012 | Mosier et al. |
| 2014/0004571 | A1 | 1/2014 | Garrett et al. |
| 2014/0273127 | A1 | 9/2014 | Fuchs et al. |

FOREIGN PATENT DOCUMENTS

| | | |
|---|---|---|
| CA | 2660990 A1 | 8/2009 |
| CA | 2666152 A1 | 4/2010 |
| CA | 2654306 C | 10/2013 |
| EP | 0 098 490 A2 | 1/1984 |
| JP | 9-507386 A | 7/1997 |
| JP | 11-172262 A | 6/1999 |
| JP | 11-506934 A | 6/1999 |
| JP | 3042076 B2 | 3/2000 |
| JP | 3042076 B2 | 5/2000 |
| JP | 2002-059118 A | 2/2002 |
| JP | 2002-105466 A | 4/2002 |
| JP | 2003-219900 A | 8/2003 |
| JP | 2003-311141 A | 11/2003 |
| JP | 2004-105855 A | 4/2004 |
| JP | 2005-027541 A | 2/2005 |
| JP | 2005-168335 A | 6/2005 |
| JP | 2005-205252 A | 8/2005 |
| JP | 2005-229821 A | 9/2005 |
| JP | 2005-534343 A | 11/2005 |
| JP | 2006-036977 A | 2/2006 |
| JP | 2006-136263 A | 6/2006 |
| JP | 2006-223152 A | 8/2006 |
| JP | 2006-289164 A | 10/2006 |
| JP | 2007-112880 A | 5/2007 |
| JP | 2007-202560 A | 8/2007 |
| JP | 2007-301472 A | 11/2007 |
| JP | 2008-054608 A | 3/2008 |
| JP | 2008-104452 A | 5/2008 |
| JP | 2008-278825 A | 11/2008 |
| JP | 2009-183153 A | 8/2009 |
| JP | 2009-183154 A | 8/2009 |
| JP | 2009-183805 A | 8/2009 |
| JP | 2010-17084 A | 1/2010 |
| JP | 4764527 B1 | 9/2011 |
| JP | 4764528 B1 | 9/2011 |
| WO | 84/03304 A1 | 8/1984 |
| WO | 95/17517 A1 | 6/1995 |
| WO | 96/18590 A1 | 6/1996 |
| WO | 96/40970 A1 | 12/1996 |
| WO | 2004/037973 A2 | 5/2004 |
| WO | 2009/096060 A1 | 8/2009 |
| WO | 2009/096061 A1 | 8/2009 |
| WO | 2009/096062 A1 | 8/2009 |
| WO | 2009/124240 A1 | 10/2009 |
| WO | 2010/038302 A1 | 4/2010 |

OTHER PUBLICATIONS

"Nikkei Biotechnology & Business," Sep. 2002; pp. 52-61.
International Search Report of PCT/JP2008/067040, date of mailing date Dec. 16, 2008.
International Search Report of PCT/JP2008/067039 (corresponding to U.S. Appl. No. 12/865,273), Mailing Date of Dec. 16, 2008.
Japanese Office Action dated Dec. 15, 2009, issued in corresponding Japanese Patent Application No. 2008-023185 (corresponding to U.S. Appl. No. 12/865,273), with English translation.
Olsson et al. "Fermentation of lignocellulosic hydrolysates for ethanol production", Enzyme and Microbial Technology. 1996; vol. 18, pp. 312-331.
Garrote et al., "Hydrothermal processing of lignocellulosic materials", Holz als Roh-und Werkstoff. 1999; vol. 57, pp. 191-202.
Ando et al. "Decomposition behavior of plant biomass in hot-compressed water", Industrial and Engineering Chemistry Research, 2000; vol. 39, pp. 3688-3693.
Mosier et al. "Features of promising technologies for pretreatment of lignocellulosic biomass", Bioresource Technology 2005; vol. 96, pp. 673-686.
Japanese Office Action dated Oct. 23, 2012, issued in corresponding Japanese Patent Application No. 2009-252201, with English translation.
Canadian Office Action dated Oct. 3, 2012, issued in Canadian Patent Application No. 2,660,990.
Canadian Office Action dated Feb. 16, 2012, issued in Canadian Patent Application No. 2,660,990.
International Search Report of PCT/JP2008/067038, date of mailing date Nov. 10, 2008.
International Search Report of PCT/JP2008/067038, date of mailing date Nov. 18, 2008.
Canadian Notice of Allowance dated Aug. 22, 2013, issued in corresponding Canadian Patent Application No. 2,713,529.

(56) References Cited

OTHER PUBLICATIONS

Indonesian Notice of Allowance dated Jun. 26, 2013, issued in corresponding Indonesian Patent Application No. W-00200902415, w/English translation.
English translation of JP 2009-183805 previously filed on Mar. 31, 2011, cited in U.S. Office Action U.S. Appl. No. 13/782,545.
Canadian Notice of Allowance dated Aug. 22, 2013, issued in corresponding Canadian Patent Application No. 266152.
Canadian Notice of Allowance dated Aug. 22, 2013, issued in corresponding Canadian Patent Application No. 2713529.
U.S. Office Action dated Oct. 28, 2013, issued in U.S. Appl. No. 12/443,515.
U.S. Office Action dated Oct. 7, 2013, issued in corresponding U.S. Appl. No. 13/700,753.
U.S. Restriction/Elections dated Aug. 22, 2013, issued in corresponding U.S. Appl. No. 13/700,753.
U.S. Office Action dated Aug. 19, 2013 issued in U.S. Appl. No. 13/578,116.
Arroyo-Lopez, F.N. et al., "Effects of temperature, pH and sugar concentration on the growth parameters of *Saccharomyces cerevisiae, S. kudriavzevii* and their interspecific hybrid", International Journal of Food Microbiology, vol. 131, pp. 120-127 (2009).
Turton, L.J. et al., "Effect of Glucose Concentration in the Growth Medium Upon Neutral and Acidic Fermentation End-products of Clostridium Bifermentans, Clostridium Sporogenes and Peptostreptococcus Anaerobius", J. Med. Microbiol., vol. 16, pp. 61-67 (1983).
Dien, B.S. et al., "Fermentation of hexose and pentose sugars using a novel ethanologenic *Escherichia coli* strain", Enzyme and Microbial Technology, vol. 23, pp. 366-371 (1998).
U.S. Office Action dated Oct. 3, 2013, issued in U.S. Appl. No. 13/782,545.
US Office Action dated Dec. 14, 2010, issued in U.S. Appl. No. 12/443,515.
US Office Action dated Mar. 29, 2011, issued in U.S. Appl. No. 12/443,515.
Examiner's Answer to Appeal Brief dated Nov. 9, 2011, issued in U.S. Appl. No. 12/443,515.
US Office Action dated Mar. 11, 2013 issued in U.S. Appl. No. 12/443,515.
Canadian Office Action dated Sep. 20, 2012, issued in Canadian Patent Application No. 2,654,306.
Canadian Office Action dated Feb. 25, 2013, issued in Canadian Patent Application No. 2,654,306.
Canadian Office Action dated Apr. 10, 2012, issued in Canadian Patent Application No. 2,713,529.
Canadian Notice of Allowance dated Jun. 26, 2013, issued in corresponding Canadian Patent Application No. 2,654,306 (1 page).
Canadian Notice of Allowance dated Jul. 2, 2013, issued in corresponding Canadian Patent Application No. 2,660,990 (1 page).
US Office Action dated Apr. 27, 2012, issued in U.S. Appl. No. 12/865,273.
US Office Action dated Jun. 25, 2012, issued in U.S. Appl. No. 12/865,273.
US Office Action dated Dec. 4, 2012, issued in U.S. Appl. No. 12/865,273.
US Office Action dated Jun. 4, 2013, issued in U.S. Appl. No. 12/865,273.
Anneli Nilsson, "Control of fermentation of lignocellulosic hydrolysates", Department of Chemical Engineering II, Lund University, Sweden (6 pages).
"Biomass-Extensive Use of Bioresources," Japanese Society for Bioscience, Biotechnology, and Agrochemistry, Asakura Publishing Co., Ltd.; Sep. 1985; pp. 90-93.
International Search Report of PCT/JP2006/319660; date of mailing Jan. 9, 2007.
"Nikkei Biotechnology & Business Biomas Ethanol," Sep. 2002; pp. 52-61.

Japanese Office Action dated Oct. 23, 2012, issued in corresponding Japanese Patent Application No. 2009-245963, with English translation (5 pages).
Canadian Office Action dated Mar. 7, 2012, issued in corresponding Canadian Patent Application No. 2,654,306 (3 pages).
Japanese Office Action dated Oct. 23, 2012, issued in corresponding Japanese Patent Application No. 2009-245963 (5 pages).
Kumagai Satoshi et al. "Fractionation and Saccharification of Cellulose and Hemicellulose in Rice Hull by Hot-Compressed-Water Treatment with Two-Step Heating", Journal of the Japan Institute of Energy, Dec. 1, 2004, vol. 83, pp. 776-781, Cited in Notice of Acceptance dated Mar. 4, 2014, issued in Japanese Patent Application No. 2009-252201.
US Final Office Action dated Feb. 13, 2014, issued in U.S. Appl. No. 12/865,273 (26 pages).
Liu, Chaogang, et al., "Continuous Fermentation of Hemicellulose Sugars and Cellulose to Ethanol", International Symposia on Alcohol Fuels, (2005), pp. 1-28 (cited in U.S. Final Office Action dated Feb. 13, 2014, issued in U.S. Appl. No. 12/865,273).
U.S. Non-Final Office Action issued Mar. 10, 2014, in related U.S. Appl. No. 13/782,545 (27 pages).
Decision of a Patent Grant dated Mar. 4, 2014, issued in JP2009-252201 (corresponding to U.S. Appl. No. 12/443,515), w/English translation (4 pages).
Decision of a Patent Grant dated Mar. 4, 2014, issued in JP2009-245963 (corresponding to U.S. Appl No. 12/438,792) w/English translation (4 pages).
Australian Notice of Acceptance dated Mar. 17, 2014, issued in Australian patent application No. 2011355013 (corresponding to U.S. Appl. No. 13/578,116) (2 pages).
U.S. Office Action dated Apr. 14, 2014, issued in U.S. Appl. No. 12/443,515 (16 pages).
Canadian Office Action dated Mar. 31, 2014, issued in Canadian Patent Application No. 2,750,753 (3 pages) (corresponding to U.S. Appl. No. 13/203,929).
U.S. Final Office Action dated May 22, 2014, issued in U.S. Appl. No. 13/700,753 (40 pages).
U.S. Final Office Action dated Jun. 3, 2014, issued in U.S. Appl. No. 13/203,9296 (22 pages).
Canadian Office Action dated Nov. 8, 2013, issued in Canadian Patent Application No. 2,801,383 (2 pages).
Canadian Notice of Allowance dated Jan. 13, 2014, issued in Canadian Patent Application No. 2,744,522 (1 page).
Indonesian Notice of Allowance dated Nov. 15, 2013, issued in Indonesian Patent Application No. W-00201002623, w/English translation, (5 pages).
U.S. Non-Final Office Action dated Dec. 17, 2013, issued in U.S. Appl. No. 13/203,929 (23 pages).
U.S. Non-Final Office Action dated Dec. 16, 2013, issued in U.S. Appl. No. 13/132,034 (29 pages).
U.S. Non-Final Office Action dated Jan. 30, 2014, issued in U.S. Appl. No. 13/578,116 (22 pages).
Gregg, D. et al., "Bioconversion of Lignocellulosic Residue to Ethanol: Process Flowsheet Development", Biomass and Bioenergy, 1995, vol. 9, No. 1-5, pp. 287-302, Cited in U.S. Office Action dated Dec. 17, 2013.
U.S. Final Office Action dated Jul. 3, 2014, issued in U.S. Appl. No. 13/578,116 (17 pages).
U.S. Final Office Action dated Aug. 18, 2014, issued in U.S. Appl. No. 13/132,034 (30 pages).
U.S. Non-Final Office Action dated Aug. 27, 2014, issued in U.S. Appl. No. 13/132,040 (53 pages).
U.S. Final Office Action dated Jul. 22, 2014, issued in U.S. Appl. No. 12/443,515 (13 pages).
Genta, M. et al., "Suinetsu Bunkaiho to Koso Bunkaiho o Kumiawaseta Nogyo Zansa To no Cellulose Biomass no Tei Cost Toka Gijutsu no Kaihatsu", Heisei 21 Nendo Biomass Energy Kanren Jigyo Seika Hokokukai, Feb. 11, 2010, pp. 55-69, URL, http://www.nedo.go.jp/events/report/FF_00003.html, Cited in JP Office Action dated Oct. 14, 2014.

(56) References Cited

OTHER PUBLICATIONS

Lehrburger, E. "Developing biorefineries to produce energy, ethanol and other industrial products", PureVision Technology, Inc., Alternative Energy Conference, Mar. 3, 2005, pp. 1-26, Cited in U.S. Office Action dated Nov. 6, 2014.
U.S. Office Action dated Sep. 30, 2014, issued in U.S. Appl. No. 13/782,545 (43 pages).
U.S. Office Action dated Nov. 6, 2014, issued in U.S. Appl. No. 12/865,273 (27 pages).
Japanese Office Action dated Oct. 14, 2014, issued in Japanese Patent Application No. 2010-154233 (corresponds to U.S. Appl. No. 13/700,753), with English Translation (7 pages).
U.S. Office Action dated Dec. 5, 2014, issued in U.S. Appl. No. 13/121,969.
Canadian Notice of Allowance dated Dec. 5, 2014, issued in Canadian Patent Application No. 2750754 (corresponds to U.S. Appl. No. 13/203,848).
Indonesian Office Action dated Oct. 29, 2014, issued in Indonesian Patent Application No. W00201103522 (corresponds to U.S. Appl. No. 13/203,929), w/English translation.
U.S. Notice of Allowance dated Nov. 5, 2014, issued in U.S. Appl. No. 12/443,515.
U.S. Office Action dated Dec. 26, 2014, issued in U.S. Appl. No. 13/132,040.
Indonesian Office Action dated Nov. 7, 2014, issued in corresponding IDW-00200902414, w|English translation (6 pages).
Indonesian Office Action dated Nov. 14, 2014, issued in IDW-00201102352, w/English translation (corresponds to U.S. Appl. No. 13/121,969) (7 pages).
International Search Report dated Jul. 3, 2012 issued in International Application No. PCT/JP2012/058460 (corresponds to U.S. Appl. No. 14/381,511).
Written Opinion of the International Searching Authority dated Jul. 3, 2012 issued in International Application No. PCT/JP2012/058460 (corresponds to U.S. Appl. No. 14/381,511).
Decision of a Patent Grant dated Nov. 12, 2013, issued in Japanese Patent Application No. 2013-536355, w/English translation (corresponds to U.S. Appl. No. 14/381,511) (4 pages).
U.S. Office Action dated Apr. 24, 2015, issued in U.S. Appl. No. 14/381,511 (20 pages).
Notice of Allowance and Fee(s) Due dated Feb. 17, 2015, issued in U.S. Appl. No. 13/782,545 (20 pages).
U.S. Office Action dated Mar. 19, 2015, issued in U.S. Appl. No. 13/121,969 (21 pages).
U.S. Office Action dated Mar. 13, 2015, issued in U.S. Appl. No. 13/722,385 (41 pages).
Notice of Allowance and Fee(s) Due dated Apr. 2, 2015, issued in U.S. Appl. No. 13/132,040 (17 pages).
U.S. Office Action dated Mar. 31, 2015, issued in U.S. Appl. No. 12/865,273 (25 pages).
Final Office Action dated Aug. 6, 2015, issued in U.S. Appl. No. 14/381,511 (14 pages).
Notice of Allowance dated Aug. 12, 2015, issued in U.S. Appl. No. 13/578,116 (48 pages).
Non-Final Office Action dated Aug. 21, 2015, issued in U.S. Appl. No. 13/203,929 (18 pages).
Notice of Allowance dated Jul. 6, 2015, issued in Indonesian application No. W-00201103522 (counterpart of U.S. Appl. No. 13/203,929) with English translation (4 pages).
Non-Final Office Action dated Sep. 25, 2015, issued in U.S. Appl. No. 13/132,034 (39 pages).
Final Office Action dated Sep. 28, 2015, issued in U.S. Appl. No. 13/203,848 (34 pages).
Final Office Action dated Sep. 28, 2015, issued in U.S. Appl. No. 13/722,385 (20 pages).
Notice of Allowance dated Sep. 30, 2015, issued in counterpart Canadian Application No. 2,719,665 (1 page).
Decision of a Patent Grant dated Nov. 10, 2015, issued in Japanese Application No. 2010-154233, with English Translation (5 pages).
Non-Final Office Action dated Jun. 19, 2015, issued in U.S. Appl. No. 13/700,753 (34 pages).

\* cited by examiner

BIOMASS HYDROTHERMAL DECOMPOSITION APPARATUS AND METHOD

The present invention relates to a biomass hydrothermal decomposition apparatus and a method thereof that enable efficient hydrothermal decomposition of biomass material, and to an organic material production system using biomass material, which system enables efficient production of organic materials such as alcohols, substitutes for petroleum, or amino acids by using such apparatus and method.

BACKGROUND ART

Technologies for producing ethanol or the like have been commercialized that involve converting woody biomass or other biomass into sugars with dilute sulfuric acid or concentrated sulfuric acid, and then subjecting them to solid-liquid separation, neutralizing the liquid phase thereof, and utilizing the resultant components as biomass materials for ethanol fermentation or the like (Patent Documents 1 and 2). Further, by using sugar as starting material, production of chemical industrial raw material (e.g., lactic fermentation) has been considered. Biomass as used herein refers to a living organism integrated in material circulation in the global biosphere or accumulation of organic materials derived from living organisms (see JIS K 3600 1258).

Sugarcane, corn, and other materials, currently used as alcohol raw materials, have been originally used for food. Using such food resources as long-term stable industrial resources is not preferable in view of life cycle of valuable food.

For this reason, it is a challenge to efficiently use cellulose resources such as herbaceous biomass and woody biomass, which are considered as potentially useful resources.

Cellulose resources include cellulose ranging from 38% to 50%, hemicelluloses components ranging from 23% to 32%, and lignin components, which are not used as fermentation materials, ranging from 15% to 22%. Due to many challenges, the industrial studies have been conducted targeting certain fixed materials, and no technologies have been disclosed yet on production systems taking into account diversity of the materials.

Production systems targeting fixed materials see almost no point regarding countermeasures for waste problems and global warming, because those systems have attempted such countermeasures with a method that brings more disadvantages to fermentation materials than starch materials. Thus, there has been a need for a method applicable to a variety of wastes in broader sense. Enzymatic saccharification methods are also considered as a future challenge due to its low efficiency. Acid treatment only achieves a low saccharification rate of about 75% (a basis for components that can be saccharified), due to excessive decomposition of sugar. Thus, the ethanol yield achieves only 25% by weight of cellulose resources (Non-Patent Document 1 and Patent Document 3).

[Patent Document 1] Japanese Patent Application Laid-open No. 9-507386
[Patent Document 2] Japanese Patent Application Laid-open No 11-506934
[Patent Document 3] Japanese Patent Application Laid-open No. 2005-168335
[Non-Patent Document 1] Nikkei Biotechnology & Business, p. 52, September 2002
[Non-Patent Document 2] Biomass-Extensive Use of Bioresources, edited by Japanese Society for Bioscience, Biotechnology, and Agrochemistry, Asakura Publishing Co., Ltd., September 1985

DISCLOSURE OF INVENTION

Problem to be Solved by the Invention

In the proposals disclosed in Patent Documents 1 and 2 above, sulfuric acid necessary for reaction needs to be constantly supplied from outside the reaction system. With increasing the production scale, this poses problems, such as increasing the cost for purchasing equipment resistant to the acid and large amounts of sulfuric acid, while increasing the cost for disposing used sulfuric acid (e.g., cost for processing with a gypsum desulfulation), and the cost for recovering such sulfuric acid.

The proposal disclosed in Patent Document 3 above involves subjecting various types of cellulose resources to hydrothermal treatment, and converting them into sugars with enzymatic saccharification. During the hydrothermal treatment, cellulase inhibitors such as lignin components (Non-Patent Document 2) that inhibit enzymatic saccharification of cellulose are not removed and mixed with cellulose. This poses a problem of reducing the efficiency in cellulose enzymatic saccharification.

Other than cellulose, hemicellulose components are also contained in cellulose resources. This poses a problem that enzymes respectively suitable for cellulose and hemicellulose components are necessary for enzymatic saccharification.

The resulting sugar solution includes a hexose solution from cellulose, and a pentose solution from hemicellulose components. For example, for alcohol fermentation, yeasts suitable for the respective solutions are necessary. Thus, alcohol fermentation needs to be improved low efficiency for fermenting a mixture of a hexose solution and a pentose solution.

As such, conventional technologies have caused a phenomenon that side reaction products inhibit enzymatic saccharification, reducing the sugar yield. Thus, what has been needed is a hydrothermal decomposition apparatus that removes inhibitors for enzymatic saccharification and thereby improves enzymatic saccharification of cellulose-based components.

In view of the foregoing problems, the present invention has an object to provide: a biomass hydrothermal decomposition apparatus and a method thereof that enable separation of cellulose-based components from biomass material; and an organic material production system using biomass material, which can efficiently produce a sugar solution using such apparatus and method, and can efficiently produce various types of organic materials (e.g., alcohols, substitutes for petroleum, or amino acids) using the sugar solution as a base material.

Means for Solving Problem

According to an aspect of the present invention, a biomass hydrothermal decomposition apparatus includes: a biomass feeder that feeds biomass material under normal pressure to under increased pressure; a hydrothermal decomposition device that allows the fed biomass material to be conveyed inside a device main body from either end thereof with a screw unit, and also allows hot compressed water to be fed from an other end of a feed section for the biomass material into the main body, so as to cause the biomass material and the hot compressed water to countercurrently contact with each other and undergo hydrothermal decomposition, and that transfers a lignin component and a hemicellulose component into the hot compressed water, so as to separate the lignin component and the hemicellulose component from the biomass material; and a biomass discharger that discharges, from an upper end of the device main body, a biomass solid residue under increased pressure to under normal pressure.

Advantageously, in the biomass hydrothermal decomposition apparatus, the conveying screw unit includes a scraper that prevents occlusion of an outlet for discharged hot water.

Advantageously, in the biomass hydrothermal decomposition apparatus, the hydrothermal decomposition device has a reaction temperature ranging from 180° C. to 240° C. and has a condition of hot compressed water.

Advantageously, in the biomass hydrothermal decomposition apparatus, a weight ratio of the fed biomass material to the fed hot compressed water is within 1:1 to 1:10.

According to another aspect of the present invention, a method for biomass hydrothermal decomposition includes: feeding biomass material under normal pressure to under increased pressure; allowing the fed biomass material to be conveyed inside a device main body from either end thereof with a screw unit, and also allowing hot compressed water to be fed from an other end of a feed section for the biomass material into the main body, so as to cause the biomass material and the hot compressed water to countercurrently contact with each other and undergo hydrothermal decomposition; transferring a lignin component and a hemicellulose component into the hot compressed water, so as to separate the lignin component and the hemicellulose component from the biomass material; and discharging, from an upper end of the device main body, a biomass solid residue under increased pressure to under normal pressure.

Advantageously, an organic material production system using biomass material includes: a pretreatment device that pretreats the biomass material; the hydrothermal decomposition apparatus of the present inventions; a first enzymatic hydrolysis device that treats, with an enzyme, cellulose in the biomass solid residue discharged from the hydrothermal decomposition device, so as to enzymatically hydrolyze the cellulose to a sugar solution containing hexose; and a fermenter that produces, using the sugar solution obtained by the first enzymatic hydrolysis device, any one of alcohols, substitutes for petroleum, or amino acids by fermentation.

Advantageously, the organic material production system using biomass material, includes: a second enzymatic hydrolysis device that treats, with an enzyme, a hemicellulose component in discharged hot water, so as to enzymatically hydrolyze the hemicellulose component to a sugar solution containing pentose; and a fermenter that produces, using the sugar solution obtained by the second enzymatic hydrolysis device, any one of alcohols, substitutes for petroleum, or amino acids by fermentation.

Effect of the Invention

According to the present invention, with use of a hydrothermal decomposition apparatus that causes biomass material conveyed by a screw and hot compressed water to countercurrently contact with each other, side reaction products (lignin components and hemicellulose components) resulting from the reaction for producing a target component, i.e., cellulose, (that is enzymatically saccharified to a hexose solution) are transferred into the hot compressed water. In this way, the cellulose-based biomass solid residue can be obtained. Accordingly, by efficiently saccharifying it to the hexose solution and using the sugar solution as a substrate material, various types of organic materials (e.g., alcohols, substitutes for petroleum, or amino acids) can be produced efficiently.

By causing biomass material and hot compressed water to countercurrently contact with each other, their components are sequentially discharged to the outside the reaction system in order of solubility in the hot water. Further, due to the temperature gradient from a portion where the biomass is fed to a portion where the hot water is fed, excessive decomposition of hemicellulose components is prevented. As a result, pentose components can be recovered efficiently.

EXPLANATIONS OF LETTERS OR NUMERALS

Figure 1:
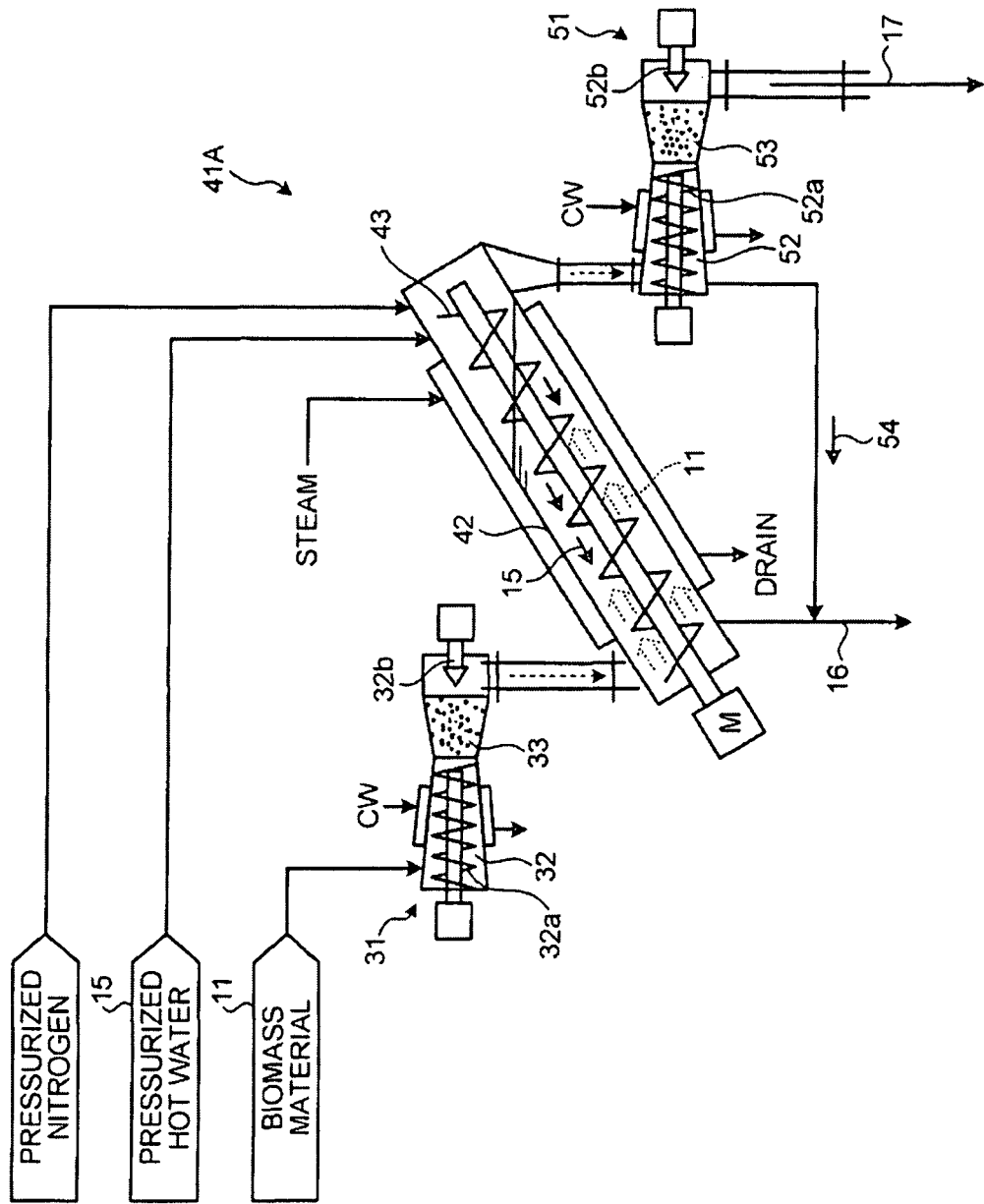
FIG. 1 is a schematic of a hydrothermal decomposition apparatus according to a first embodiment.

11 biomass material
12 pretreatment device
13 pulverized biomass
15 hot compressed water
16 discharged hot water
17 biomass solid residue
18 enzyme
19 enzymatic hydrolysis device
19-1 first enzymatic hydrolysis device
19-2 second enzymatic hydrolysis device
20-1 first sugar solution (hexose)
20-2 second sugar solution (pentose)
23 ethanol
41A to 41D hydrothermal decomposition apparatus

BEST MODE(S) FOR CARRYING OUT THE INVENTION

Exemplary embodiments of the present invention are described with reference to the accompanying drawings. The present invention is not limited to the embodiments. Constituting elements in the embodiments include elements easily achieved by a person skilled in the art, or elements being substantially equivalent to those elements.

First Embodiment

A biomass hydrothermal decomposition apparatus according to an embodiment of the present invention is described with reference to the drawings. FIG. 1 is a schematic of a biomass hydrothermal decomposition apparatus according to the embodiment. As shown in FIG. 1, a biomass hydrothermal decomposition apparatus 41A according to the present embodiment includes: a biomass feeder 31 that feeds a biomass material 11 under normal pressure to under increased pressure; the hydrothermal decomposition apparatus 41A that allows the fed biomass material (e.g., straw in the present embodiment) 11 to be gradually conveyed inside a gradient device main body (hereinafter, "device main body") 42 from a lower end thereof with a conveyor screw 43, and also allows hot compressed water 15 to be fed into the device main body 42 from an upper end thereof, which is different from a feed section for the biomass material 11, so as to cause the biomass material 11 and the hot compressed water 15 to countercurrently contact with each other and undergo hydrothermal decomposition, and that transfers lignin components and hemicellulose components into the hot compressed water 15, so as to separate the lignin components and the hemicellulose components from the biomass material 11; and a biomass discharger 51 that discharges a biomass solid residue 17 under increased pressure to under normal pressure, at the upper and of the device main body 42.

In the present embodiment, the biomass material 11 is fed from the lower end. The present invention is not limited to this, and the biomass material 11 may be fed from the upper end reversely. In this case, the hot compressed water 15 is fed from the lower end. Examples of the biomass feeder 31 that feeds biomass under normal pressure to under increased pressure may include a pump unit such as a piston pump or a slurry pump.

Figure 2:
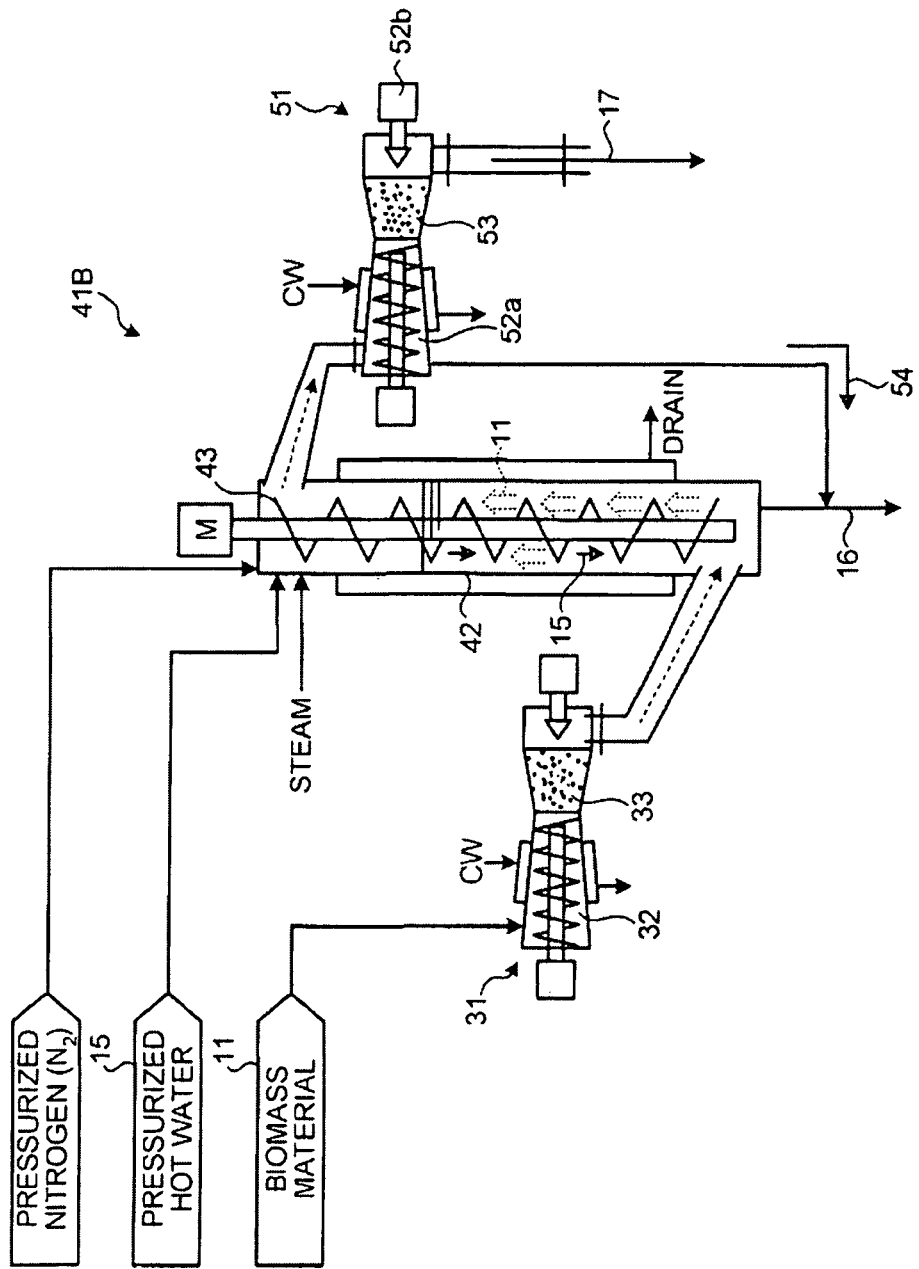
FIG. 2 is a schematic of another hydrothermal decomposition apparatus according to a first embodiment.

In the present embodiment, the hydrothermal decomposition apparatus 41A is a gradient type apparatus as shown in FIG. 1. The present invention is not limited to this, and a vertical hydrothermal decomposition apparatus 41B may be adopted, as shown in FIG. 2. Alternatively, a horizontal hydrothermal decomposition reactor may be adopted.

The apparatus may be arranged as a gradient type or a vertical type, because it is preferable regarding that the gas resulting from the hydrothermal decomposition reaction, the gas brought into the feedstock, and the like can be released quickly from the upper side. This arrangement is also preferable in view of the discharging efficiency, because decomposed products are discharged with the hot compressed water 15 and therefore the concentration of the discharged materials is increased from the upper side to the lower side.

By providing the conveyor screw 43, 1) the delivery of the solid is possible by the counter-current flow of solid and liquid, 2) the solid-liquid separation is possible inside the device main body 42, and 3) the hot compressed water on the surface of the solid and inside the solid is progressively mixed inside the device main body 42, so that the reaction is facilitated.

Figure 3:
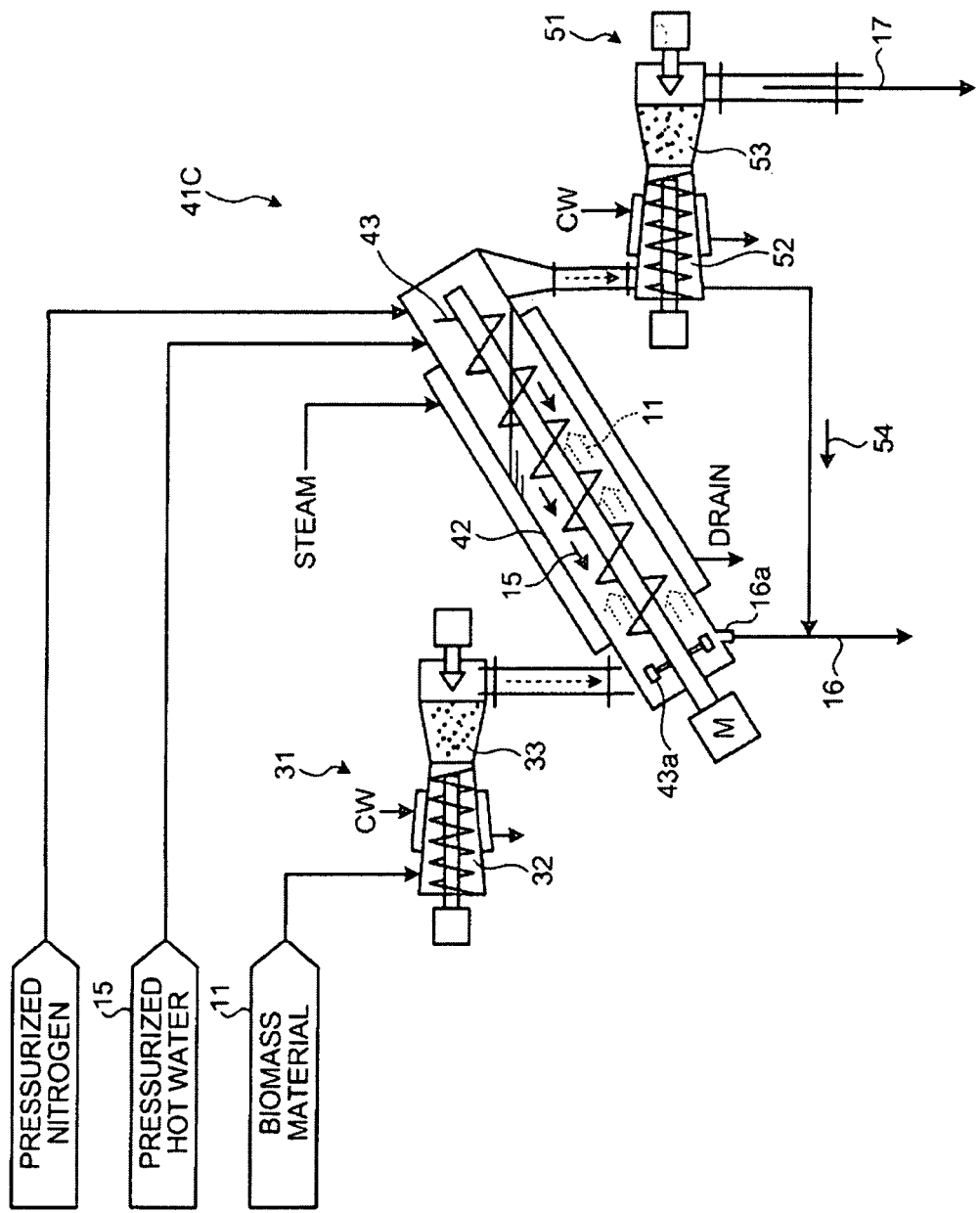
FIG. 3 is a schematic of another hydrothermal decomposition apparatus according to a first embodiment.

As shown in a hydrothermal decomposition apparatus 41C in FIG. 3, the conveyor screw 43 may include a scraper 43a that prevents occlusion of an outlet 16a for discharged hot water 16.

Biomass to be fed to the hydrothermal decomposition apparatus 41 is not limited to any specific type, and is a living organism integrated in material circulation in global biosphere or accumulation of organic materials derived from living organisms (see JIS K 3600 1258), in the present invention, particularly, lignocellulose resources of wood materials such as broadleaf trees and plant materials; agricultural wastes; and food wastes are preferably used.

The biomass material 11 is preferably broken into particles having a diameter of 5 millimeters or less, though not limited to this particle diameter. In the present embodiment, biomass may be subjected to pretreatment with pretreatment equipment such as pulverizing equipment, before being fed. In addition, biomass may be cleaned with cleaning equipment. When the biomass material 11 is rice husk for example, the biomass material 11 can be fed to the hydrothermal decomposition apparatus 41A, without being subjected to pulverization.

In the hydrothermal decomposition apparatus 41A, the reaction temperature ranges from 180° C. to 240° C. preferably, and from 200° C. to 230° C. more preferably. This is because, at temperatures below 180° C., the hydrothermal decomposition takes place at a low rate and requires a longer time, increasing the apparatus size, which are not preferable. On the contrary, at temperatures above 240° C., the decomposition rate is too high and more cellulose components are transferred from the solid phase to the liquid phase, facilitating excessive decomposition of hemicellulose sugars, which are not preferable. Dissolution of hemicellulose components, starts at about 140° C., dissolution of cellulose starts at about 230° C., and dissolution of lignin components starts at about 140° C. The temperature is preferably set within a range from 180° C. to 240° C. that allows cellulose to be remained in the biomass solid residue, and that enables hemicellulose components and lignin components to be decomposed at adequate rates.

The reaction pressure is preferably set to a pressure higher by 0.1 MPa to 0.5 MPa than the saturated vapor pressure of water at each temperature, which allows the hot compressed water to stay inside the device main body. The reaction time is preferably three minutes to ten minutes, not more than 20 minutes. This is because a longer reaction time increases the ratio of excessively decomposed products and is not preferable.

According to the present invention, for the flowage of the hot compressed water 15 and the flowage of the biomass material 11 inside the device main body 42A of the hydrothermal decomposition apparatus 41-1A, the hot compressed water 15 and the biomass material 11 are countercurrently contacted, preferably stirred and flowed by so called countercurrent flow.

In the hydrothermal decomposition apparatus, the solid of the biomass material 11 is fed from the left side in the figure, while the hot compressed water 15 is fed from the right side in the figure. Because the biomass material 11 and the hot compressed water 15 move in an opposite direction to one another, the hot compressed water 15 (hot water, the liquid dissolving decomposed products) is moved while being soaked in solid particles by the counter-current flow against the solid, the biomass material 11.

When countercurrently contacting each other, the solid biomass material 11 is decomposed with the hot compressed water 15, and the resulting decomposed products are dissolved and transferred to the hot compressed water 15.

As a ratio of the solid to the liquid, the liquid ratio is preferably less, because it enables reduction in amount of water to be recovered and in amount of steam used for heating water. The weight ratio of the biomass material to the hot compressed water both to be fed is, for example, 1:1 to 1:10 preferably, and 1:1 to 1:5 more preferably, though it varies accordingly depending on the apparatus configuration.

According to the present embodiment, in a slurry transport reactor that mixes the biomass material 11 and water in advance and feeds the mixture into the device main body, water needs to be added in large amounts (10 times to 20 times in weight ratio) relative to the solid so as to provide flowability to the slurry. However, because the feedstock, i.e., the biomass material 11, and the hot compressed water 15 for removing lignin components and hemicellulose components in the biomass are fed into the hydrothermal decomposition apparatus 41A with separate systems, the weight ratio of the liquid can be made small relative to that of the solid, thus improving economic efficiency.

According to the present invention, because a gas portion is present inside the device main body 42, pressurized nitrogen (N$_2$) is fed inside.

Inside the hydrothermal decomposition apparatus 41A, the temperature of the biomass material 11 is increased by causing it to contact the hot compressed water 15 in the device main body 42 and directly exchanging the heat. The temperature may be increased by using steam or the like from the outside as necessary.

The biomass feeder 31 employs a screw feeding mechanism 32 that has a material seal mechanism realized by the biomass itself, and feeds the solid biomass material 11 under normal pressure to under increased pressure. Specifically, with the feeding mechanism 32 including a screw feeder 32a and a hydraulic cylinder 32b, the biomass material 11 fed inside is compressed, so that a biomass plug 33 is formed. The biomass plug 33 serves as a material seal for keeping the pressure inside the hydrothermal decomposition apparatus. Gradually pressed by the screw feeder 32a, the biomass can be gradually discharged from an edge of the hydraulic cylinder 32b, so that the biomass material 11 is reliably fed into the device main body 42.

The biomass discharger 51 has a similar configuration to that of the biomass feeder 31. With a feeding mechanism including a screw feeder 52a and a hydraulic cylinder 52b, the biomass solid residue 17 reacted in the hydrothermal decomposition apparatus is compressed, so that a biomass plug 53 is formed. The biomass plug 53 serves as a material seal for keeping the pressure inside the hydrothermal decomposition apparatus. The biomass solid residue 17 under increased pressure, from which lignin components and hemicellulose components have been transferred to the discharged hot water 16, can be discharged to under normal pressure. When the biomass solid residue 17 compressed, the residual water is removed from the biomass plug 53. This dewatered solution 54 includes components soluble in hot compressed water (lignin components and hemicellulose components). Thus, the dewatered solution 54 is sent to the discharged hot water 16 and treated together with the discharged hot water 16.

Because the pressure is changed from increased pressure to normal pressure inside the biomass discharger 51, the biomass solid residue 17 to be discharged is steam-exploded, causing breakage of its fiber structure. This improves the efficiency of enzymatic saccharification in the subsequent process.

The biomass discharger 51 can remove both enzymatic saccharification inhibitors and ethanol fermentation inhibitors, or either of them, which are low-molecular-weight volatile inhibitors.

In the present invention, by causing biomass material and hot compressed water to countercurrently contact with each other, their components are sequentially discharged in order of solubility in the hot water. Further, due to the concentration gradient and the temperature gradient from where the biomass is fed to where the hot water is fed, excessive decomposition of hemicellulose components is prevented. As a result, pentose components can be recovered, efficiently. Further, by causing the biomass material and the hot compressed water to countercurrently contact with each other, the heat is recovered, which is preferable in view of system efficiency.

Figure 4:
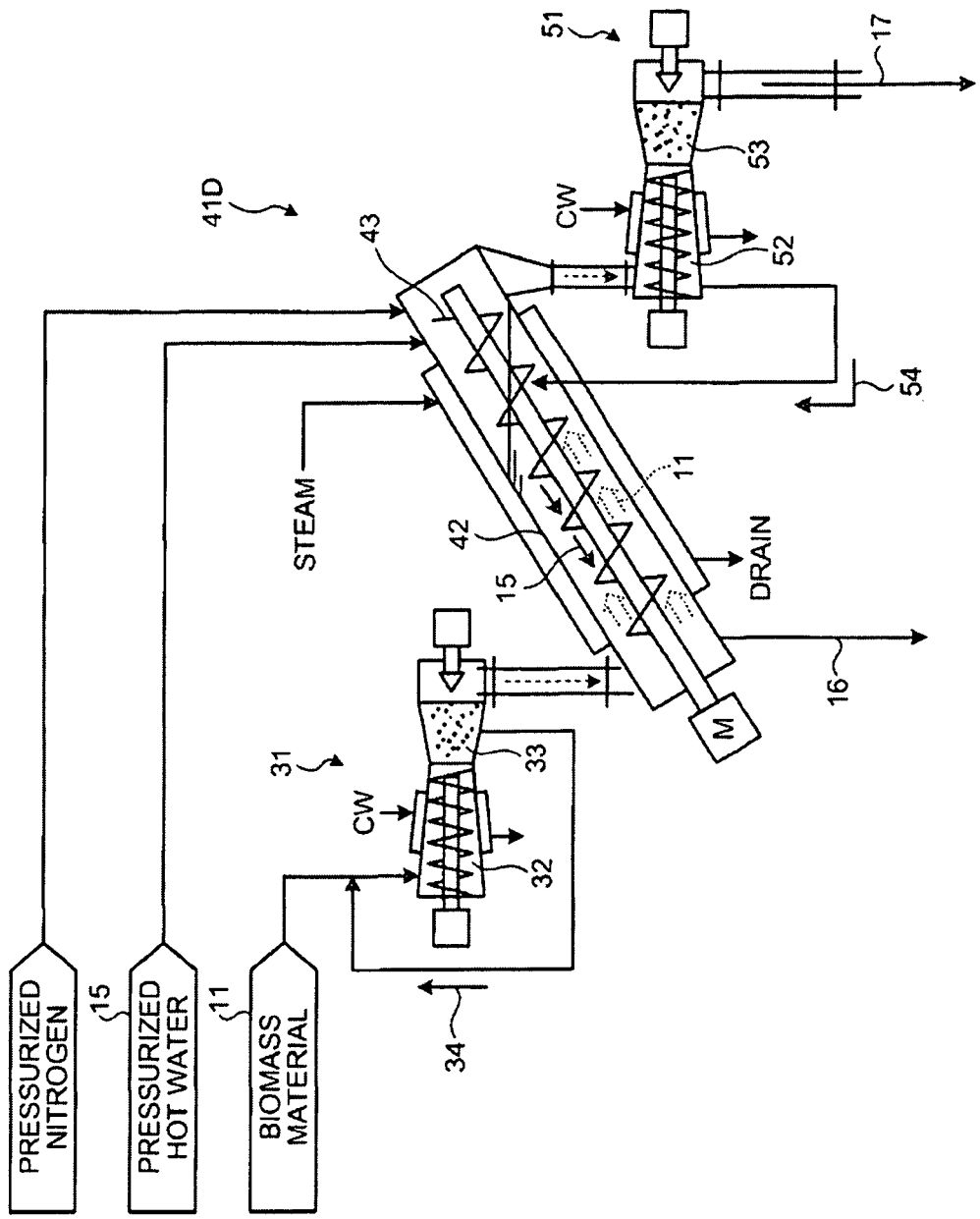
FIG. 4 is a schematic of another hydrothermal decomposition apparatus according to a first embodiment.

In a hydrothermal decomposition apparatus 41O shown in FIG. 4, the dewatered solution 54, separated in the biomass discharger 51, may be fed again into the device main body 42. This arrangement reduces the amount of the hot compressed water to be fed into the apparatus. Further, a desirable counter-current flow is realized.

As shown in FIG. 4, a hydrothermal decomposition apparatus 41D includes an excess water removal line 32, so that excess water 34 contained in the biomass is removed from the section for feeding the biomass material 11 into the device main body 42A. The excess water 34 may be used to make the biomass material 11 wet.

Second Embodiment

Figure 5:
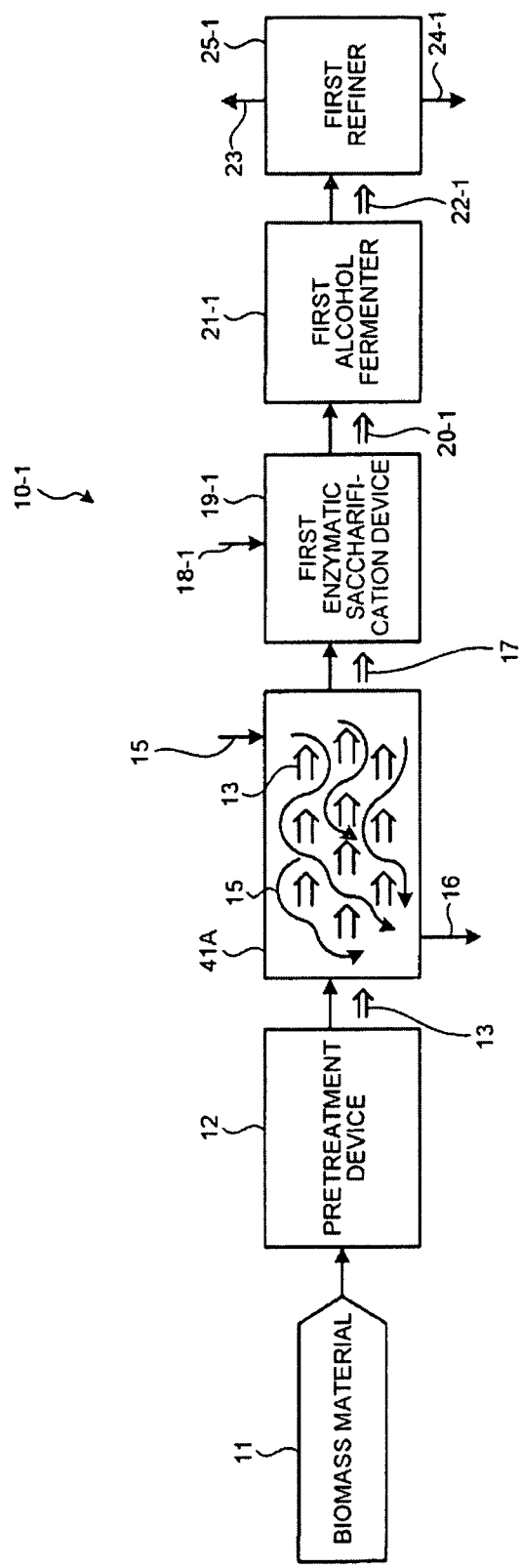
FIG. 5 is a schematic of an alcohol production system according to a second embodiment.

With reference to the drawings, the following describes a system of producing an organic material, i.e., alcohol, with use of biomass material according to a second embodiment of the present invention. FIG. 5 is a schematic of an organic material production system using biomass material according to the embodiment. As shown in FIG. 5 an alcohol production system 10-1 using biomass material according to the present embodiment includes: a pretreatment device 12 that pulverizes the biomass material 11; the hydrothermal decomposition apparatus 41A (shown in FIG. 1) that hydrothermally decomposes pulverized biomass 13 by causing it to countercurrently contact the hot compressed water 15, transfers lignin components and hemicellulose components into the hot compressed water 15, and separates the lignin components and the hemicellulose components from the biomass; a first enzymatic hydrolysis device 19-1 that treats cellulose in the biomass solid residue 17, discharged from the hydrothermal decomposition apparatus 41A, with an enzyme (cellulase) 18-1 to enzymatically hydrolyze it to a sugar solution containing hexose; a first alcohol fermenter 21-1 that produces an alcohol (ethanol in the present embodiment) by fermentation using a first sugar solution (hexose) 20-1 obtained by the first enzymatic hydrolysis device 19-1; and a first refiner 25-1 that refines a first alcohol fermentation liquid 22-1, so as to separate it into a target product, i.e., ethanol 23, and a residue 24-1.

According to the present invention, in the hydrothermal decomposition apparatus 41A shown in FIG. 1, use of the counter-current flow transfers lignin components and hemicellulose components to the liquid phase, i.e., the hot compressed water 15, while allowing cellulose to remain in the solid phase, i.e., the biomass solid residue 17. In this way, the first sugar solution (hexose) 20-1 is obtained at the first enzymatic hydrolysis device 19-1 for performing enzymatic saccharification. Accordingly, it is possible to establish a fermentation process suitable for a hexose (fermentation suitable for an end product: in the present embodiment, fermentation for obtaining the ethanol 23 using the first alcohol fermenter 21-1).

Although the present embodiment describes an example that an alcohol, ethanol, is obtained by fermentation, the present invention is not limited to this example. Other than alcohols, substitutes for petroleum used as chemical product material, or amino acids used as food and feed materials can be obtained with a fermenter.

Examples of industrial products produced from a sugar solution as a substrate material may include liquefied petroleum gas (LPG), auto fuel, aircraft jet fuel, heating oil, diesel oil, various types of heavy oils, fuel gas, naphtha, and naphtha decomposed products such as ethylene glycol, ethanolamine, alcohol ethoxylate, vinyl chloride polymer, alkylaluminum, polyvinyl acetate (PVA), vinyl acetate emulsion, polystyrene, polyethylene, polypropylene, polycarbonate, methyl methacrylate (MMA) resin, nylon, and polyester. Thus, substitutes for industrial products derived from crude oil, which is fossil fuel, and sugar solution derived from biomass, which is a feedstock for producing such substitutes, can be used efficiently.

Third Embodiment

Figure 6:
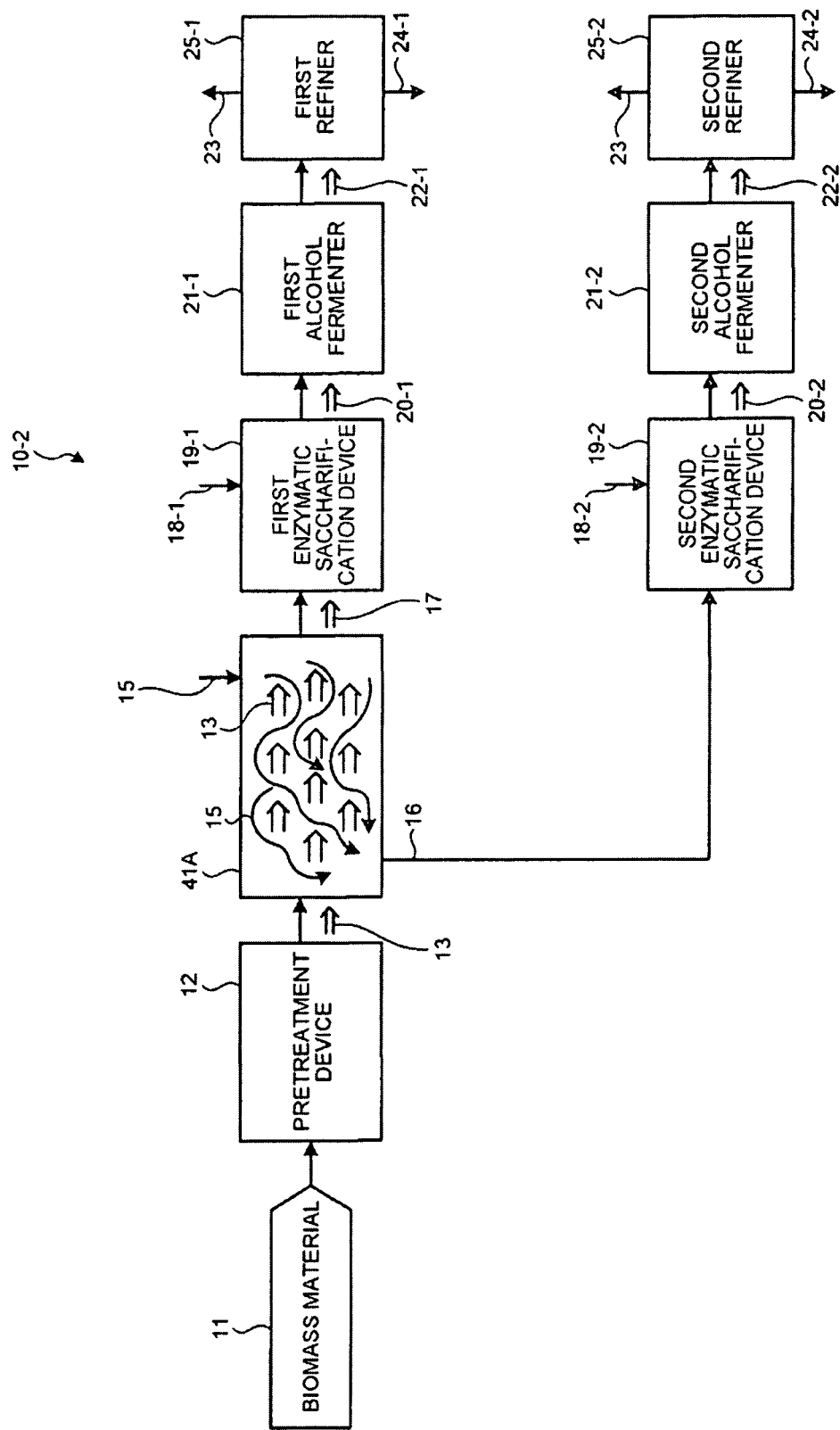
FIG. 6 is a schematic of an alcohol production system according to a third embodiment.

With reference to the drawings, the following describes a system of producing an organic material, i.e., alcohol, with use of biomass material according to a third embodiment of the present invention. FIG. 6 is a schematic of a system of producing an organic material, i.e., alcohol, with use of biomass material according to the present embodiment. As shown in FIG. 6, an alcohol production system 10-2 using biomass material according to the present embodiment is constituted by the alcohol production system 10-1 shown in FIG. 5 that includes a second enzymatic hydrolysis device 19-2. The second enzymatic hydrolysis device 19-2 treats hemicellulose components, transferred into the hot water 16 discharged from the hydrothermal decomposition apparatus 41A, with an enzyme to enzymatically hydrolyze it to a second sugar solution 20-2 containing pentose. Two enzymatic hydrolysis devices, two alcohol fermenters, and two refiners are provided (the first enzymatic hydrolysis device 19-1, the second enzymatic hydrolysis device 19-2, the first alcohol fermenter 21-1, a second alcohol, fermenter 21-2, the first refiner 25-1, and a second refiner 25-2). The ethanol 23 is obtained by performing an enzymatic hydrolysis process, an alcohol fermentation process, and an alcohol refining process that are suitable for each of the first sugar solution (hexose) 20-1 and a second sugar solution (pentose) 20-2.

In the present embodiment, the ethanol 23 can be produced by fermentation, using the second sugar solution (pentose) 20-2 obtained by the second enzymatic hydrolysis device 19-2.

The discharged hot water is not necessarily treated in a separate system. For example, processes subsequent to the enzymatic hydrolysis devices, processes subsequent to the alcohol fermenters, or processes subsequent to the refiners may be arranged as common processes, or other modification may be made appropriately.

According to the present invention, in the hydrothermal decomposition apparatus 4Th, use of the counter-current flow allows cellulose to remain in the solid phase which is the biomass solid residue 17. Accordingly, the first sugar solution (hexose) 20-1 is obtained by the first enzymatic hydrolysis device 19-1 for performing enzymatic saccharification. Further, hemicellulose components dissolved in the liquid phase which is the hot compressed water 15, are separated as the discharged hot water 16, and the second sugar solution (pentose) 20-2 is obtained by the second enzymatic hydrolysis device 19-2. This enables the solid and the liquid to be separated efficiently and saccharified in different processes. Accordingly, fermentation processes suitable for hexose and pentose (fermentation suitable for an end product: e.g., ethanol fermentation) can be established.

As such, in the hydrothermal decomposition apparatus 41A, use of the counter-current flow transfers a side reaction product and a lignin component soluble in hot compressed water, both acting as inhibitors during enzymatic saccharification reaction for obtaining hexose, to the hot compressed water 15. Accordingly, the cellulose-based biomass solid residue 17 is obtained, improving the yield of hexose in the subsequent enzymatic saccharification reaction.

On the other hand, hemicellulose components contained in the separated discharged hot water 16 is saccharified later at the second enzymatic hydrolysis device 19-2, so that a sugar solution containing pentose can be obtained. Then, by using yeasts etc. suitable for hexose and pentose, ethanol can be obtained by fermentation individually and efficiently.

As described above, the present invention provides: a biomass hydrothermal decomposition apparatus and a method that can produce, by transferring cellulose based components and hemicellulose components from the biomass material to the hot compressed water and separating them from each other, sugar solutions suitable for the cellulose-based components and the hemicellulose components (hexose sugar solution and pentose sugar solution), and that can efficiently produce, using the sugar solutions as substrate materials, various types of organic materials (e.g., alcohols, substitutes for petroleum, or amino acids); and an organic material production system using biomass material. However, a conventional technology causes a phenomenon that a side reaction product inhibits enzymatic saccharification and a sugar yield is reduced.

INDUSTRIAL APPLICABILITY

As described, according to the present invention, a hydrothermal decomposition apparatus separates cellulose-based components from biomass material, so as to efficiently produce a sugar solution. Further, using the sugar solution as a substrate material, various types of organic materials (e.g., alcohols, substitutes for petroleum, or amino acids) can be efficiently produced.

The invention claimed is:
1. A biomass hydrothermal decomposition apparatus comprising:
a biomass feeder that includes:
 a biomass feeder inlet that receives the biomass material containing cellulose, hemicellulose, and lignin;
 a screw feeder and a hydraulic cylinder that compress the biomass material between the screw feeder and the hydraulic cylinder; and
 a biomass feeder outlet that discharges the compressed biomass material;
a discharging pipe that discharges water from the compressed biomass material from the biomass feeder;
a hydrothermal decomposition device consisting essentially of:
 a device main body that countercurrently contacts the compressed biomass material with a decomposition liquid consisting essentially of hot compressed water, hydrothermally decomposes the compressed biomass so as to elute a lignin component and a hemicellulose component into the hot compressed water and obtain a hot water containing the lignin component and the hemicellulose component and a biomass solid containing cellulose-based components,
 a biomass material inlet that is directly connected to the biomass feeder outlet of the biomass feeder, provided on one side of the device main body and supplies the compressed biomass material from the biomass feeder into the device main body,
 a biomass solid residue outlet that is provided on the other side of the device main body that discharges the hydrothermally decomposed biomass material as the biomass solid residue from the device main body,
 a conveyor screw unit that is provided in the device main body and conveys the compressed biomass material from the biomass material inlet to the biomass solid residue outlet,
 a hot compressed water inlet that is provided on other side of the device main body and supplies the decomposition liquid into the device main body,
 a discharged hot water outlet that is provided on a side wall of the one side of the device main body and discharges the hot water containing the lignin component and the hemicellulose component as a discharged hot water from the device main body, and
 optionally a gas inlet,
a biomass discharger that has a biomass solid residue inlet directly connected to the biomass solid residue outlet of the hydrothermal decomposition device, receives the biomass solid residue from the biomass solid residue outlet and discharges the biomass solid residue from an increased pressure to a decreased pressure, wherein the conveyor screw unit has;
- a drive shaft;
- a conveyor screw that is provided on the drive shaft and conveys the compressed biomass material; and
- a scraper that is provided on the drive shaft and associated with the discharged hot water outlet so as to prevent occlusion of the discharged hot water outlet and wherein the hydrothermal decomposition device has a reaction temperature ranging from 180° C. to 240° C. and has a condition of hot compressed water.

2. The biomass hydrothermal decomposition apparatus according to claim 1, wherein a weight ratio of the fed biomass material to the fed hot compressed water is within 1:1 to 1:10.

3. The biomass hydrothermal decomposition apparatus according to claim 1, wherein a pressure is higher than saturated vapor pressure of water at each temperature of the reaction temperature by 0.1 MPa to 0.5 MPa.

4. The biomass hydrothermal decomposition apparatus according to claim 1, wherein the hydrothermal decomposition apparatus is a gradient type or a vertical type.

5. The biomass hydrothermal decomposition apparatus according to claim 1, wherein the reaction temperature is increased by using steam.

6. The biomass hydrothermal decomposition apparatus according to claim 1, wherein the gas inlet is a pressurized nitrogen inlet.

7. An organic material production system using biomass material, the organic material production system comprising:
- a pretreatment device that pretreats the biomass material containing cellulose, hemicellulose, and lignin;
- the hydrothermal decomposition apparatus according to claim 1;
- a first enzymatic hydrolysis device that treats, with an enzyme, cellulose in the biomass solid residue discharged from the hydrothermal decomposition device, so as to enzymatically hydrolyze the cellulose to a sugar solution containing hexose; and
- a fermenter that produces, using the sugar solution obtained by the first enzymatic hydrolysis device, any one of alcohols, substitutes for petroleum, or amino acids by fermentation.

8. A method for biomass hydrothermal decomposition comprising:
- compressing biomass material containing cellulose, hemicellulose, and lignin and discharging the biomass material;
- discharging water from the biomass material;
- directly supplying the biomass material into one side of a hydrothermal decomposition device to undergo hydrothermal decomposition, wherein the hydrothermal decomposition consists essentially of;
  - supplying a decomposition liquid consisting essentially of hot compressed water into the other side of the hydrothermal decomposition device;
  - conveying the biomass material from the one side to the other side of the hydrothermal decomposition device with a conveyor screw unit, wherein the conveyor screw unit including a drive shaft, a conveyor screw that is provided on the drive shaft and conveys the compressed biomass material, and a scraper that is provided on the drive shaft; and
  - countercurrently contacting the biomass material with the decomposition liquid and hydrothermally decomposing the biomass material, so as to elute a lignin component and a hemicellulose component into the hot compressed water and obtain a hot water containing the lignin component and the hemicelluloses component and a biomass solid containing cellulose-based components;
- discharging the hydrothermally decomposed biomass material as the biomass solid residue from the other side of the hydrothermal decomposition device;
- directly discharging the hot water containing the lignin component and the hemicelluloses component as a discharged hot water from a discharged hot water outlet that is provided on a side wall of the one side of the hydrothermal decomposition device;
- discharging the biomass solid residue from the discharged hot water outlet from an increased pressure to a decreased pressure, wherein the conveying the biomass material includes preventing occlusion of the discharged hot water outlet with a scraper of the conveyor screw unit and wherein the hydrothermal decomposition device has a reaction temperature ranging from 180° C. to 240° C. and has a condition of hot compressed water.

* * * * *